(12) United States Patent
Ouchi (10) Patent No.: US 7,347,860 B2
(45) Date of Patent: Mar. 25, 2008

(54) ENDOSCOPE FOR HIGH-FREQUENCY TREATMENT

(75) Inventor: Teruo Ouchi, Saitama-ken (JP)

(73) Assignee: PENTAX Corporation, Tokyo (JP)

(*) Notice: Subject to any disclaimer, the term of this patent is extended or adjusted under 35 U.S.C. 154(b) by 467 days.

(21) Appl. No.: 10/959,062

(22) Filed: Oct. 7, 2004

(65) Prior Publication Data

US 2005/0080411 A1   Apr. 14, 2005

(30) Foreign Application Priority Data

Oct. 8, 2003   (JP) .............................. 2003-349063

(51) Int. Cl.
   *A61B 18/18*   (2006.01)
   *A61B 1/00*    (2006.01)

(52) U.S. Cl. .................. 606/46; 600/104; 600/127

(58) Field of Classification Search ............ 606/45–47; 600/104, 127
   See application file for complete search history.

(56) References Cited

U.S. PATENT DOCUMENTS

| | | | |
|---|---|---|---|
| 6,086,583 A * | 7/2000 | Ouchi ......................... | 606/41 |
| 6,095,970 A | 8/2000 | Hidaka et al. | |
| 6,193,717 B1 | 2/2001 | Ouchi | |
| 6,394,949 B1 * | 5/2002 | Crowley et al. ............ | 600/127 |
| 6,524,234 B2 * | 2/2003 | Ouchi ......................... | 600/127 |
| 6,689,051 B2 | 2/2004 | Nakada et al. | |
| 6,689,130 B2 * | 2/2004 | Arai et al. ................... | 606/46 |
| 7,063,661 B2 * | 6/2006 | Okada ......................... | 600/127 |
| 7,122,002 B2 * | 10/2006 | Okada ......................... | 600/127 |
| 2001/0053909 A1 * | 12/2001 | Nakada et al. .............. | 606/47 |

FOREIGN PATENT DOCUMENTS

| | | |
|---|---|---|
| JP | 09-066019 | 3/1997 |
| JP | 08-187415 | 7/1997 |
| JP | 09-187415 | 7/1997 |
| JP | 2000-79086 | 3/2000 |
| JP | 2002-045369 | 2/2002 |

OTHER PUBLICATIONS

U.S. Appl. No. 10/962,606 to Ouchi, filed Oct. 13, 2004.
English Language Abstract of JP09-187415.
U.S. Appl. No. 10/922,956 to Ouchi, filed Aug. 23, 2004.

* cited by examiner

*Primary Examiner*—Michael Peffley
(74) *Attorney, Agent, or Firm*—Greenblum & Bernstein, P.L.C.

(57) ABSTRACT

An endoscope for high-frequency treatment includes a flexible inserting section and an operation unit connected thereto. At least one terminal is provided to the operation unit and is connected to a high-frequency power supply. The endoscope further includes a hood having at least one treatment electrode for the high-frequency treatment and at least one contact, which are connected with at least one conductive line. The endoscope further includes a tip unit provided to a tip end of the inserting section. The tip unit has a hood receiving portion to which the hood is detachably coupled and one power supply electrode which contacts the at least one contact of the hood when the hood is coupled to the tip unit. The at least one power supply electrode is connected with the at least one terminal provided to the operation unit through a conductive wire which is inserted in the inserting section.

13 Claims, 6 Drawing Sheets

ENDOSCOPE FOR HIGH-FREQUENCY TREATMENT

BACKGROUND OF THE INVENTION

The present invention relates to an endoscope for high-frequency treatment used for incision or excision of mucous membranes of human tissues or the like using high-frequency electric current.

For performing incision or excision of mucous membranes of human tissues, a high-frequency treatment device such as a high-frequency snare is typically used. In case that the treatment does not go well even if the high-frequency treatment tool is inserted in a treatment tool insertion channel of the endoscope, there has been suggested an improved endoscope which has a hood detachably coupled to the tip of the endoscope body, and the hood is used as a base of the high-frequency treatment tool. An example of such an endoscope is disclosed in Japanese Patent Provisional Publication No. HEI 09-187415.

In the above publication, besides channel(s) formed in the endoscope body, another channel is provided outside the endoscope and the hood, and the high-frequency snare is inserted therethrough. According to this structure, depending on the high-frequency tool, lead lines for supplying electrical current to the electrodes of the high-frequency tool mounted on the hood may be run outside the inserting section of the endoscope.

In such a case, since the lead lines are swinging around the inserting section of the endoscope, a patient who swallows the inserting section suffers from pain. The lead lines are also troublesome for an operator since they may twine his/her hand and obstruct the operation of the endoscope. However, if the lead lines are inserted into the channel for a treatment tool, other tools such as a suction tool and the like cannot be used simultaneously.

The present invention is advantageous in that an improved endoscope for high-frequency treatment is provided. The endoscope has a detachably coupled tip hood that functions as a base for the high-frequency tools, and can be used without imposing burden to both the patient and the operator.

According to an aspect of the invention, there is provided an endoscope for high-frequency treatment, which includes a flexible inserting section to be inserted in a human cavity, an operation unit connected to a proximal end of the flexible inserting section, at least one terminal, which is connected to a high-frequency power supply, being provided to the operation unit, a hood provided with at least one treatment electrode for the high-frequency treatment, at least one contact and at least one conductive line connecting the treatment electrode and the contact, and a tip unit provided at a tip end of the inserting section, the tip unit being formed with a hood receiving portion to which the hood is detachably coupled, the tip unit being provided with at least one power supply electrode which contacts the at least one contact of the hood when the hood is coupled to the tip unit, the at least one power supply electrode being connected with the at least one terminal provided to the operation unit through a conductive wire which is inserted in the inserting section.

Optionally, there may be a pair of terminals which are connected to opposite outputs of the high-frequency power supply, a pair of treatment electrodes and a pair of contacts. The pair of treatment electrodes and the pair of contacts are connected with a pair of conductive lines, respectively. Further, there may be a pair of power supply electrodes which contact the pair of contacts of the hood, the pair of power supply electrodes being connected with the pair of terminals.

Further optionally, at least one groove may be formed on the outer surface of the terminal unit, the at least one power supply electrode being provided in the groove.

Still optionally, the at least one power supply electrode may be configured to resiliently deform, and when the hood is coupled to the tip end, the power supply electrode resiliently biases the contact to retain the hood in position.

In a particular case, the at least one conductive line may be embedded in a wall of the hood.

Optionally, a part of the at least one conductive line may be exposed to inside of a wall of the hood.

Further optionally, the hood is configured to fitted on the tip unit, a step being formed on an inner wall of the hood, the step contacting the end of the tip unit to position the hood in a depth direction.

Further optionally, the hood may be a hollow cylindrical member.

DETAIL DESCRIPTION OF THE EMBODIMENTS

Referring to the accompanying drawings, embodiments of the present invention will be described.

Figure 1:
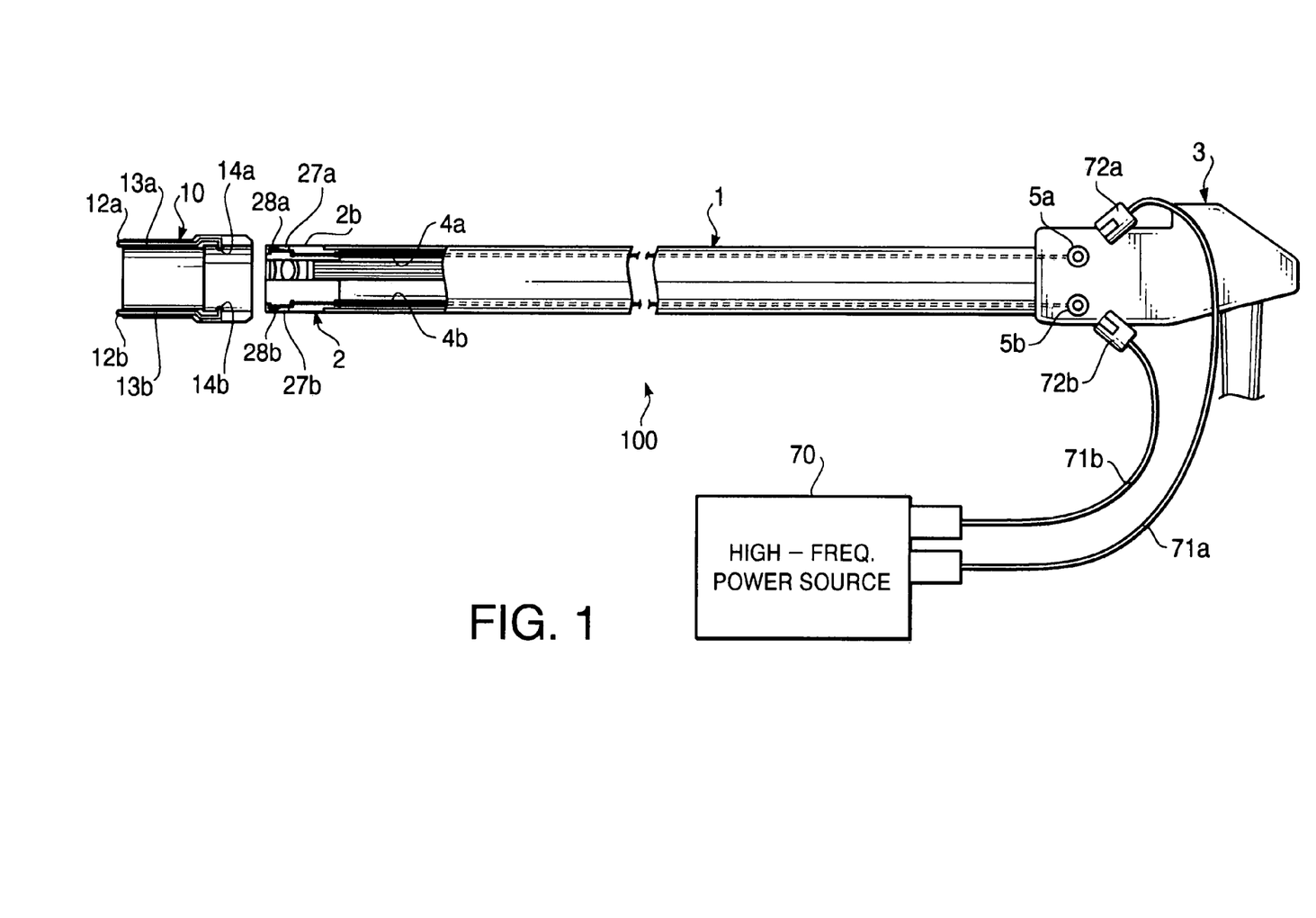
FIG. 1 is a partially cross-sectional view of an endoscope for high-frequency treatment according to a first embodiment.

FIG. 1 is a partially cross-sectional view of an endoscope 100 for high-frequency treatment according to a first embodiment of the invention.

The endoscope 100 includes a flexible inserting section 1 to be inserted in a human cavity, a tip unit 2 and an operation unit 3. The tip unit 2 is connected to the tip of the inserting section 1. The proximal end of the inserting section 1 is connected to the operation unit 3. In FIG. 1, the tip unit 2 is shown as a cross-sectional plan view, while the operation unit 3 is shown as a side view for the sake of description.

Figure 2:
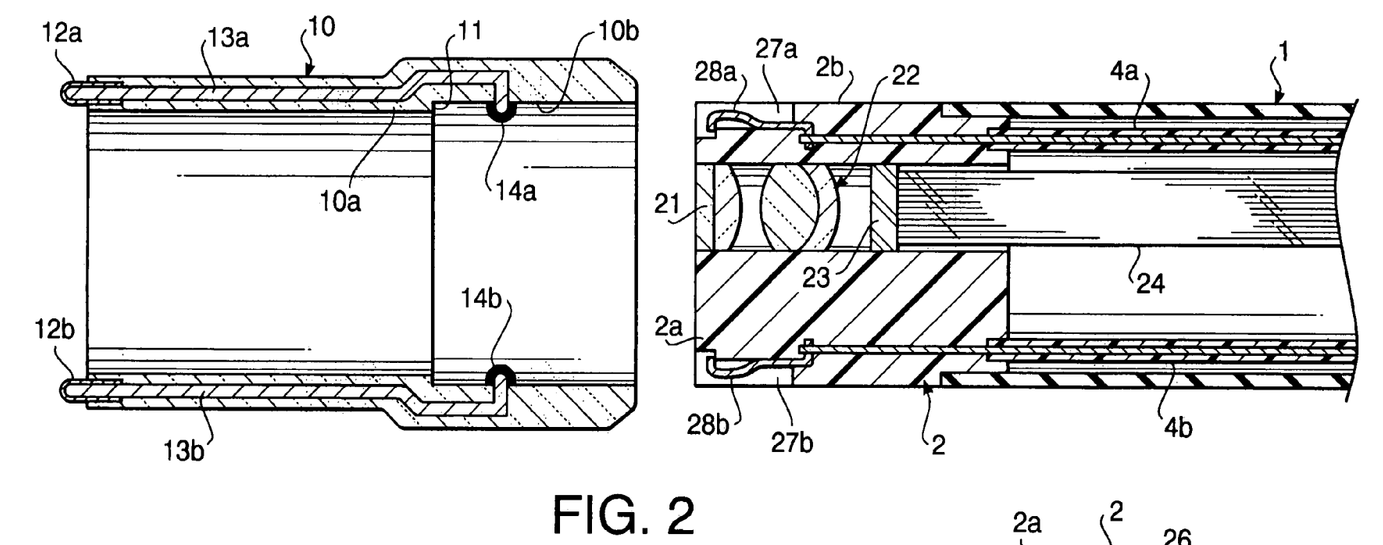
FIG. 2 is a cross-sectional plan view of a tip portion of an inserting section of the endoscope and a tip hood, which is not coupled to the endoscope, according to the first embodiment.
Figure 3:
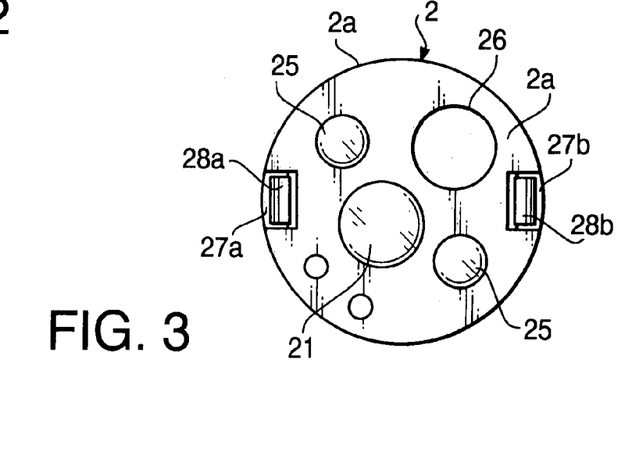
FIG. 3 is a front view of the tip of the inserting section of the endoscope according to the first embodiment.

FIG. 2 is a cross-sectional plan view of a tip portion of an inserting section 1, tip unit 2 and a tip hood 10, and FIG. 3 is a front view showing an end surface 2a of the tip unit 2 according to the first embodiment.

The tip unit 2 has a shape of a cylindrical column, and on its end surface 2a, an observation window 21 is formed. Behind (i.e., on the proximal side) of the observation window 21, an objective optical system 22 and a solid state imaging device 23 such as a CCD is provided. Light from an object to be observed is converged by the objective lens 22, thereby an image of the object being formed on an image receiving surface of the imaging device 23.

In FIG. 2, 24 denotes a signal cable that transmits an image signal generated by the imaging device 23 to a video processor (not shown) connected to the endoscope 100. It should be noted that this configuration (i.e., the imaging device and the signal cable 24 for transmitting the image signal) can be replaced with an image guide fiber bundle for transmitting the image.

As shown in FIG. 3, on the end surface 2a of the tip unit 2, an illuminating window 25 from which light for illuminating the object emerges, an outlet 26 of a treatment tool inserting channel are formed as well as the observation window 21.

Figure 4:
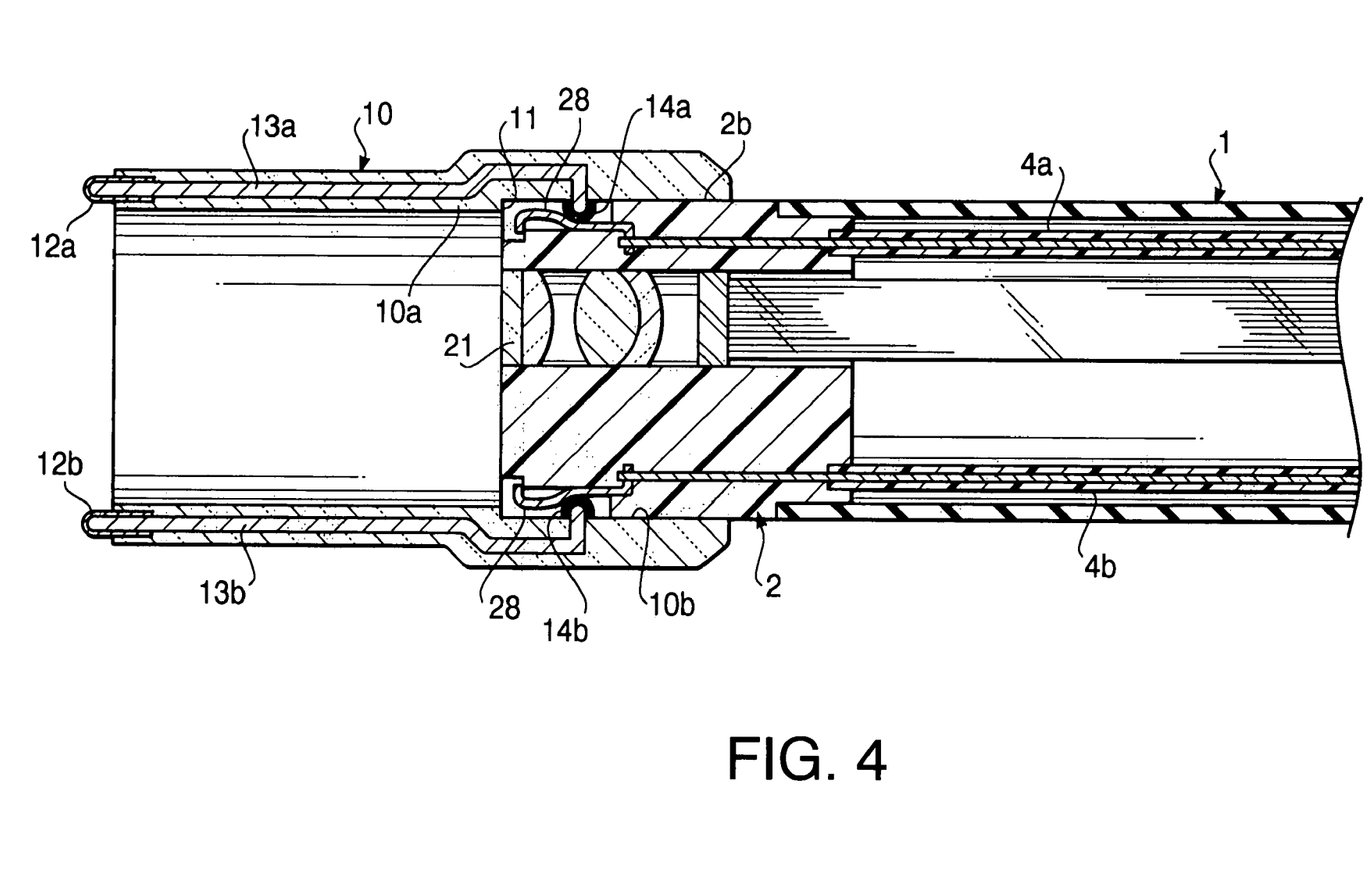
FIG. 4 is a cross-sectional plan view of the tip portion of the inserting section of the endoscope and the tip hood coupled thereto according to the first embodiment.

The tip hood 10 (see FIG. 2) can be detachable from or attachable to the tip unit 2 (attached state is shown in FIG. 4). The hood 10 is made of transparent synthetic resin such as acrylic resin or polycarbonate resin, which is formed to be a hollow cylinder shape.

FIG. 4 is a cross-sectional plan view of the tip hood 10, tip unit 2 and the tip portion of the inserting section 1 when the tip hood 10 is attached to the tip unit 2. As shown in FIG. 4, a rear-half portion (i.e., the right-hand side half portion in FIG. 4) of the tip hood 10 is fitted on an outer circumferential surface 2a of the tip unit 2. On an inner circumferential wall, a step 11 is formed such that the inner diameter of the tip hood 10 on the front side (i.e., the left-hand side in FIG. 4) of the step 11 is smaller than the inner diameter on the rear side thereof. In the following description, the smaller diameter portion of the inner surface will be referred to as a first inner surface 10a and the larger diameter portion will be referred to as a second inner surface 10b. When the tip hood 10 is fitted on the tip unit 2, the step 11 contacts the end surface 2a of the tip unit 2, thereby the tip hood 10 is located at a predetermined position with respect to the tip unit 2 in the depth direction thereof. That is, the second inner surface 10b completely fitted on the outer circumference 2b of the tip unit 2. As described above, the outer circumference 2b of the tip unit 2 serves as a hood attaching portion, to which the hood 10 can be detachably attached.

Figure 5A:
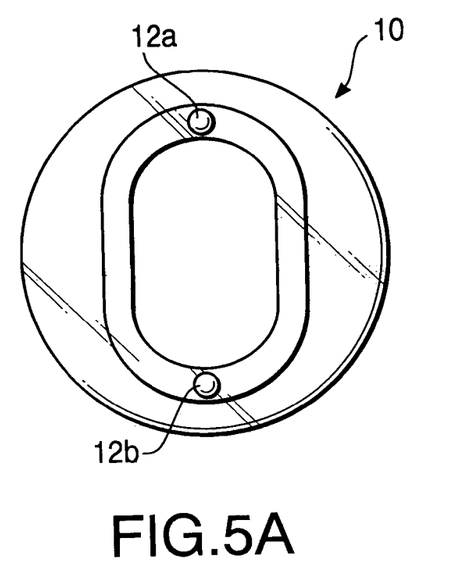
FIGS. 5A and 5B are front view and perspective view of the tip hood when coupled to the tip of the inserting section of the endoscope according to the first embodiment.
Figure 5B:
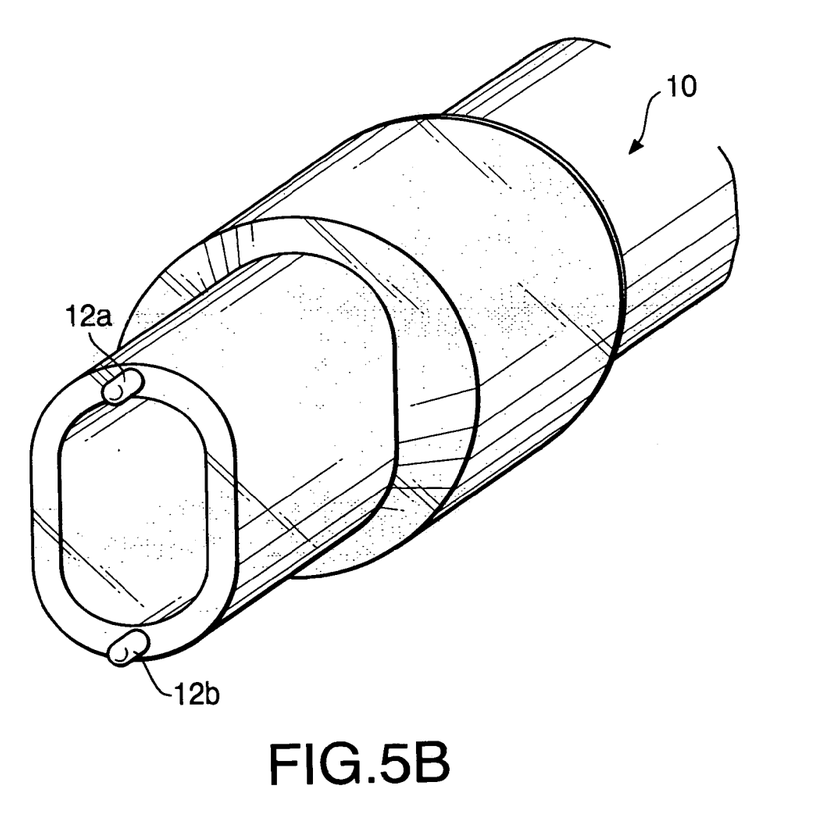

As shown in FIGS. 2, 5A and 5B, a pair of electrodes (bipolar electrodes) 12a and 12b are protruded forward from the front end surface of the tip hood 10 at right and left (i.e., at the up and down sides in FIG. 2) of the hood 10. Further, on the second inner surface 10b of the hood 10, a pair of contacts 14a and 14b are provided in the right and left direction (i.e., the up and down direction in FIG. 2). In this embodiment, the contacts 14a and 14b are spaced by 180° along the circumferential direction (i.e., provided at rotationally symmetrical positions) and protruded inwardly by a predetermined amount. The electrodes 12a, 12b and the contacts 14a, 14b are connected with a pair of conductive lines 13a, 13b, respectively. The conductive lines 13a and 13b are embedded in the hood 10 as shown in FIG. 2.

Corresponding to the contacts 14a and 14b, a pair of grooves 27a and 27b are formed on the outer circumference 2b of the tip unit 2 at the tip portion thereof as shown in FIGS. 2 and 3. The grooves 27a and 27b reach the end surface 2a, and therefore, as shown in FIG. 3, the end surface 2a has cutouts viewed from the front at portions of the grooves 27a and 27b.

In the grooves 27a and 27b, electrodes 28a and 28b are situated, respectively. The electrodes 28a and 28b contact the contacts 14a and 14b when the hood 10 is fitted on the tip unit 2. The electrodes 28a and 28b are connected to a pair of conductive wires 4a and 4b, which are inserted in the inserting section, respectively and independently.

Each of the electrodes 28a and 28b is formed from a conductive and resilient metal plate. Tip end side portions (i.e., the left-hand side portions in FIG. 2) of the electrodes 28a and 28b bulge outward so as to interfere with the contacts 14a and 14b, respectively, when the hood 10 is attached to the tip unit 2.

When the hood 10 is attached to the tip unit 2, the bulging portions of the electrodes 28a and 28b are pressed by the contacts 14a and 14b and resiliently deformed inwardly. When the hood 10 is completely fitted on the tip unit (fully inserted), as shown in FIG. 4, the electrodes 28a and 28b substantially return to their original position, with being biased by the resilient force to the contacts 14a and 14b, respectively.

According to the embodiment, the electrodes 28a and 28b realize a click stop for resiliently retaining the hood 10 in position. That is, when the hood 10 is fitted on and completely attached to the tip unit 2, the resilient force of the electrodes 28a and 28b prevents the hood 10 from being removed from the tip unit 2.

When relatively strong force is applied to draw the hood 10 forward with respect to the endoscope 100 (or the tip unit 2), the hood 10 can be drawn therefrom as the contacts 14a and 14b make the electrodes 28a and 28b deform inwardly.

The conductive wires 4a and 4b are provided with insulating coating, and inserted along the entire length of the inserting section 1.

With the above-described construction, when the hood 10 is fitted on the tip unit 2, the high-frequency electrodes 12a and 12b are connected with the conductive wires 4a and 4b via the contacts between the pair of electrodes 28a, 28b and the contacts 14a, 14b, respectively.

The proximal ends of the conductive wires 4a and 4b reach the operation unit 3 as shown in FIG. 1, and respectively connected with power terminals 5a and 5b, protruded on a side surface of the operation unit 3.

In FIG. 1, 70 denotes a high-frequency power source, to which a pair of power supply cords 71a and 71b are connected. At the ends of the power supply cords 71a and 71b, high-frequency power supply plugs 72a and 72b are connected, respectively. The power supply plugs 72a and 72b can be detachably connected to the power terminals 5a and 5b provided on the operation unit 3, respectively.

When the hood 10 is coupled to the tip unit 2, and the plugs 72a and 72b are connected to the power terminals 5a and 5b, the high-frequency electrodes 12a and 12b are connected to the high-frequency power source 70. Therefore, by supplying the high-frequency current, high-frequency treatment (e.g., incision or excision of the in vivo tissues which the high-frequency electrodes 12a and 12b contact) can be performed.

According to the structure described above, no lead lines are exposed to the outside of the endoscope 100, problems arising from the conductive wires 4a and 4b will not occur.

Since the conductive wires 4a and 4b are not inserted through the tool channel, any tool, when necessary, can be used when the high-frequency treatment is performed.

Figure 6:
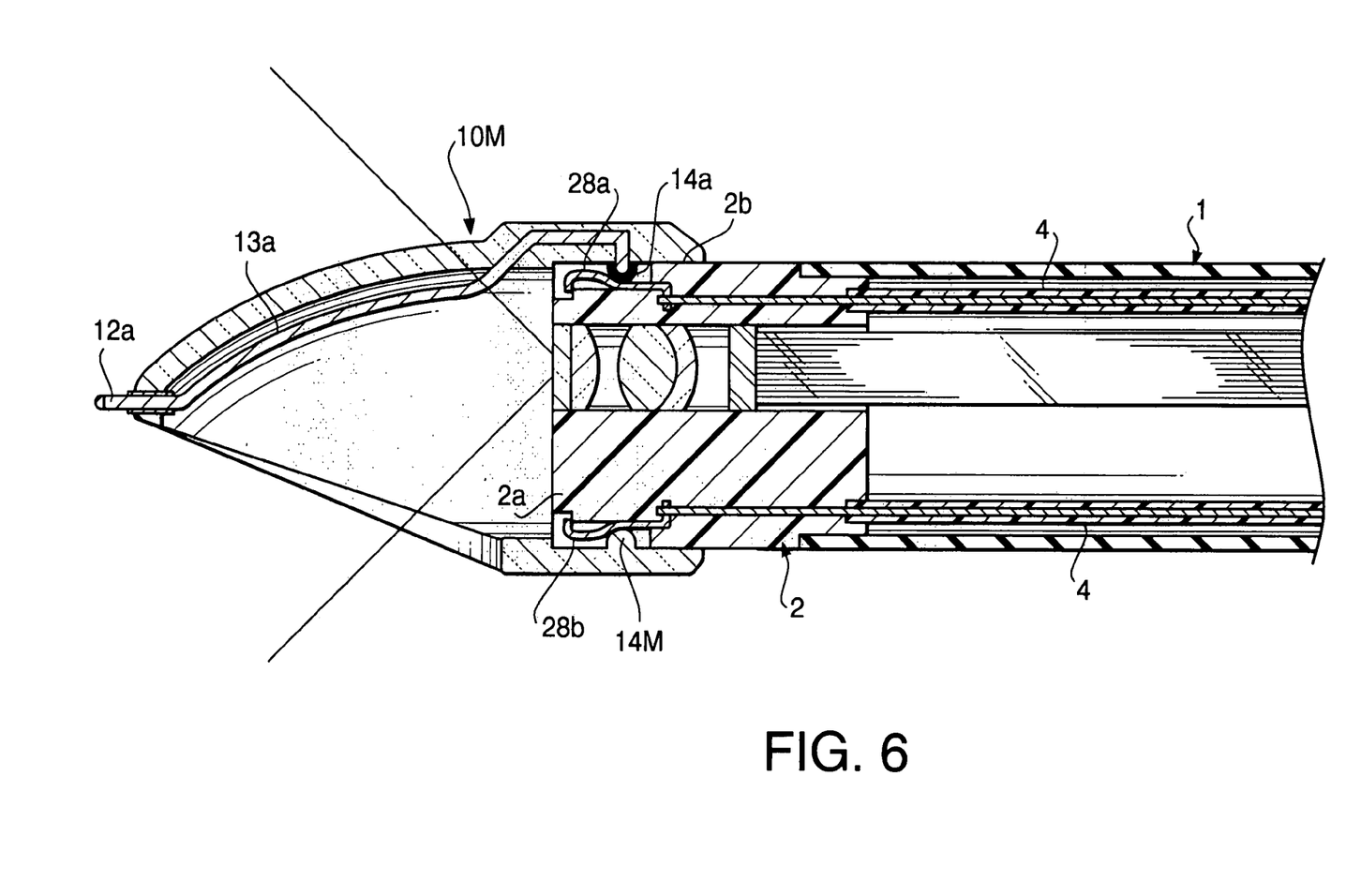
FIG. 6 is a cross-sectional view of a tip portion of an inserting section of the endoscope and a tip hood coupled thereto according to a second embodiment.
Figure 7:
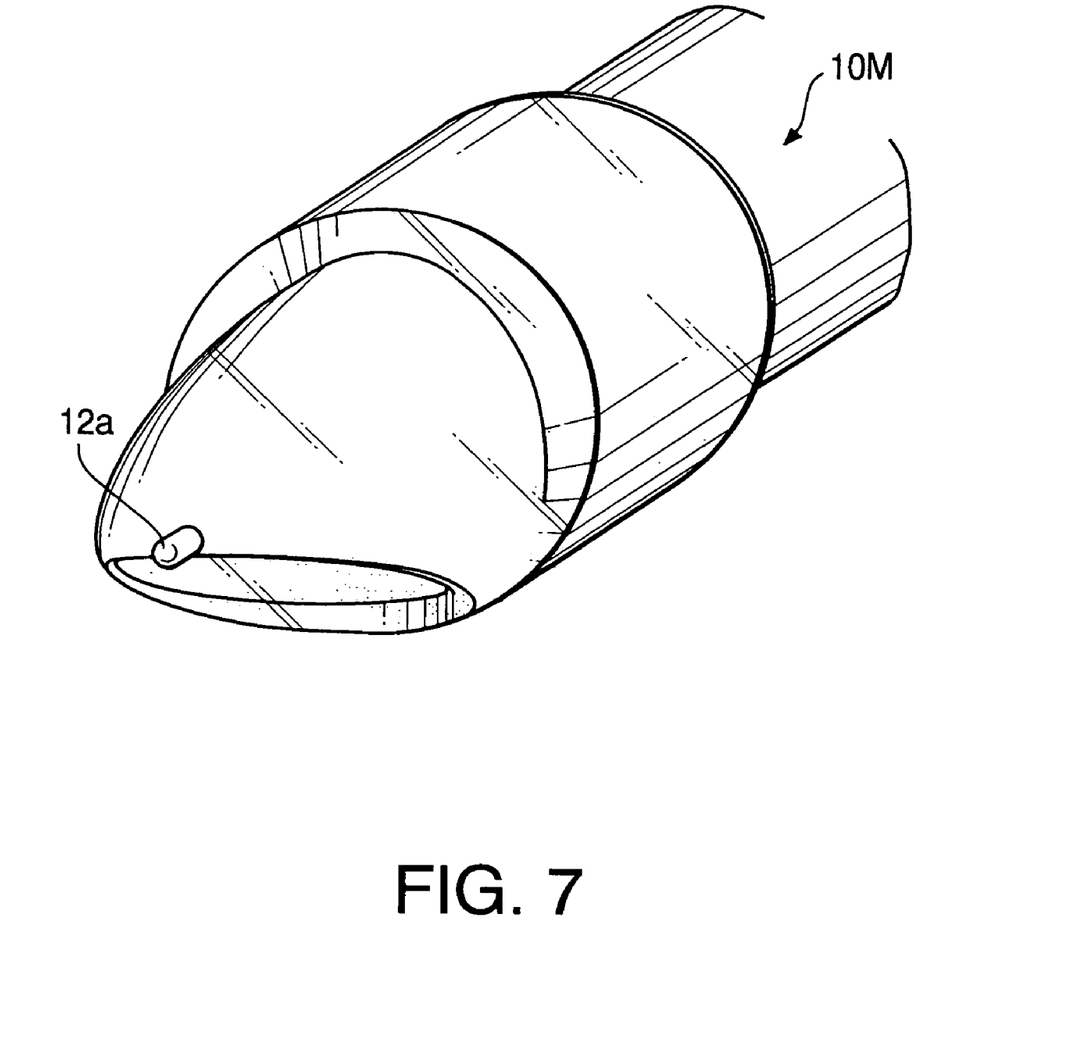
FIG. 7 is a perspective view of the tip hood according to the second embodiment.

FIG. 6 is a cross-sectional view of a tip portion of the inserting section 1, the tip unit 2 and a tip hood 10M coupled thereto according to a second embodiment. FIG. 7 is a perspective view of the tip hood 10M according to the second embodiment.

The tip hood 10M is a mono polar type hood, which has only one high-frequency electrode 12a. In this case, only one contact 14a is necessary to supply the current to the electrode 12a. However, in order to retain the hood 10M onto the tip unit 2, a dummy contact (a protrusion) 14M is formed as a protrusion formed on the inner surface 10b and protruded inwardly at a position corresponding to the electrode 28b.

In this example, the intermediate portion of the conductive line 13a is not embedded in the wall of the hood 10M but exposed to the inside of the hood.

When the mono polar type hood 10M is used, one of the power supply plugs 72a and 72b (see FIG. 1) is connected to the conductive wire 4a, while the other is connected to an opposite polar plate, which is placed outside the patient.

In the above-described embodiments, the tip unit 2 and the inserting section 1 is configured such that both of the mono polar type hood 10M and bipolar type hood 10 can be attached. The invention need not be limited to such a configuration. If the endoscope only employs a mono polar type hood 10, the tip unit and the inserting section may be configured to accept only the mono polar type hood 10M.

In the embodiments, the pair of electrodes 28a and 28b are arranged to be spaced by 180°. The invention need not be limited to such a configuration, and the positions of the electrodes 28a and 28b may be changed. In such a case, the positions of the contacts 14a and 14b (or the dummy contact 14M) may be changed corresponding to the positions of the electrodes 28a and 28b.

In each embodiment, the step 11 is formed on the inner wall of the tip hood 10 (10M) to regulate the position thereof in the depth direction of the tip unit 2. The structure can be modified such that a larger diameter portion (i.e., a flange) is formed on the outer circumference of the tip portion 2 contact the end surface of the tip hood 10 (10M) to regulate the position of thereof in the depth direction.

Alternatively, the tip hood 10 (10M) formed of elastic transparent plastic. In such a case, only by press-inserting the tip portion 2 into the tip hood, the tip hood can be firmly held in position, and the step as described above can be omitted.

The present disclosure relates to the subject matter contained in Japanese Patent Application No. 2003-349063, filed on Oct. 8, 2003, which is expressly incorporated herein by reference in its entirety.

What is claimed is:

1. An endoscope for high-frequency treatment, comprising:
   a flexible inserting section adapted to be inserted in a human cavity;
   an operation unit connected to a proximal end of the flexible inserting section, at least one terminal, which is connected to a high-frequency power supply, being provided to the operation unit;
   a hood provided with at least one treatment electrode for the high-frequency treatment, at least one contact and at least one conductive line connecting the at least one treatment electrode and the at least one contact; and
   a tip unit provided at a tip end of the inserting section, the tip unit being formed with a hood receiving portion to which the hood is detachably couples, the tip unit being provided with at least one resiliently deformable power supply electrode which contacts the at least one contact of the hood when the hood is coupled to the tip unit and is resiliently biased by the at least one contact to retain the hood in position, the at least one power supply electrode being connected with the at least one terminal provided to the operation unit through a conductive wire which is inserted in the inserting section.

2. The endoscope according to claim 1,
   wherein the at least one terminal includes a pair of terminals connected to opposite outputs of the high-frequency power supply,
   the at least one treatment electrode includes a pair of treatment electrodes,
   the at least one contact includes a pair of contacts,
   the pair of electrodes and the pair of contacts are connected with a pair of conductive lines, respectively,
   the at least one power supply electrode includes a pair of power supply electrodes which contact the pair of contacts of the hood, and
   the pair of power supply electrodes are connected with the pair of terminals.

3. The endoscope according to claim 1,
   wherein at least one groove is formed on an outer surface of the tip unit, the at least one power supply electrode being provided in the at least one groove.

4. The endoscope according to claim 1,
   wherein the at least one conductive line is embedded in a wall of the hood.

5. The endoscope according to claim 4,
   wherein a part of the at least one conductive line is exposed to an inside of a wall of the hood.

6. The endoscope according to claim 1,
   wherein the hood is configured to fit on the tip unit, a step is formed on an inner wall of the hood, and the step contacts an end of the tip unit to position the hood in a depth direction.

7. The endoscope according to claim 1, wherein the hood is a hollow cylindrical member.

8. The endoscope according to claim 1, wherein the at least one power supply electrode comprises a pair of power supply electrodes, one of the pair of power supply electrodes contacts the at least one contact of the hood, and another of the pair of power supply electrodes engages with a protrusion formed on an inner surface of the hood.

9. An endoscope for high-frequency treatment, comprising:
   a flexible inserting section adapted to be inserted in a human cavity;
   an operation unit connected to a proximal end of the flexible inserting section, at least one terminal, which is connected to a high-frequency power supply, being provided to the operation unit;
   a hood provided with at least one treatment electrode for the high-frequency treatment, at least one contact which protrudes from an inner surface of the hood, and at least one conductive line connecting the at least one treatment electrode and the at least one contact; and
   a tip unit provided at a tip end of the inserting section, the tip unit being formed with a hood receiving portion to which the hood detachably couples, the tip unit being provided with at least one power supply electrode which contacts a portion of the at least one contact of the hood protruding from the inner surface of the hood when the hood is coupled to the tip unit, the at least one power supply electrode being connected with the at least one terminal provided to the operation unit through a conductive wire which is inserted in the inserting section
   wherein the at least one power supply electrode comprises a pair of power supply electrodes, one of the pair of power supply electrodes contacts the at least one contact of the hood, and another of the pair of power supply electrodes engages with a protrusion formed on an inner surface of the hood, and the at least one contact of the hood and the protrusion resiliently bias the pair of power supply electrodes to retain the hood in position.

10. The endoscope of claim 9, wherein the hood has a hollow substantially cylindrical shape, and the at least one contact protrudes from an inner circumferential surface of the hood.

11. The endoscope of claim 9, wherein the at least one contact comprises a pair of contacts protruding into substantially opposite sides of a hollow inner area of the hood.

12. The endoscope according to claim 9, wherein at least one groove is formed on an outer surface of the tip unit, the at least one power supply electrode being provided in the at least one groove.

13. The endoscope according to claim 12, wherein the at least one groove comprises a pair of grooves formed on substantially opposite sides of the tip unit, and the at least one power supply electrode comprises a pair of power supply electrodes.

\* \* \* \* \*